United States Patent [19]

Kojima et al.

[11] Patent Number: 4,956,072
[45] Date of Patent: Sep. 11, 1990

[54] OXYGEN SENSOR

[75] Inventors: Takao Kojima, Nagoya; Yasuhiro Ujita, Kasugai, both of Japan

[73] Assignee: NGK Spark Plug Co., Ltd., Aichi, Japan

[21] Appl. No.: 356,918

[22] Filed: May 25, 1989

[51] Int. Cl.$^5$ .......................................... G01N 27/417
[52] U.S. Cl. .................................... 204/424; 204/428
[58] Field of Search ............................... 204/421–429

[56] References Cited

U.S. PATENT DOCUMENTS

| | | | |
|---|---|---|---|
| 3,909,385 | 9/1975 | Spielberg et al. | 204/427 |
| 4,597,849 | 7/1986 | Burkhardt et al. | 204/427 |
| 4,626,337 | 12/1986 | Hotta et al. | 204/427 |
| 4,818,364 | 4/1989 | Weber et al. | 204/427 |

Primary Examiner—T. Tung
Attorney, Agent, or Firm—Sughrue, Mion, Zinn, Macpeak & Seas

[57] ABSTRACT

An oxygen sensor including a detection element with electrodes for detecting an oxygen partial pressure, a metal member for containing the detection element, and an insulation spacer for supporting the detection element. The oxygen sensor further includes an insulating layer for covering the surface of a recess defined by the detection element, the metal member, and the insulating spacer, thus preventing the deterioration of insulation between the electrodes of the detection element and the metal member. The oxygen sensor of this invention can accurately detect the oxygen partial pressure for a long time.

6 Claims, 2 Drawing Sheets

OXYGEN SENSOR

BACKGROUND OF THE INVENTION

This invention relates to an oxygen sensor for detecting a partial pressure of oxygen in the surrounding atmosphere.

In combustion apparatus (e.g., an internal combustion engine), an oxygen partial pressure for the exhaust gas is detected by an oxygen sensor, and the air/fuel ratio of the gas mixture combusted in the apparatus is adjusted to a desired value. The fuel consumption rate and the emission are thus improved to attain the optimum driving conditions.

An example of general oxygen sensors (Japanese Patent Application No. S61-146210) is shown in the partially sectional view of FIG. 2. The oxygen sensor of FIG. 2 includes a detection element 16 consisting of a test-tube shaped oxygen-ion-conducting solid electrolyte 10 (e.g., $ZrO_2$) and a pair of porous electrodes 12 and 14 on each face of the electrolyte 10. The oxygen sensor has: a metal member 18; the detection element 16 mounted in the member 18 with an insulating ceramic spacer 20, packed talc powders 22, and a ceramic sleeve 24; a protection tube 26 for the detection element 16; a metal terminal 28 connected to the external electrode 12 of the detection element 16; a metal terminal 32 connected to the inner electrode 14 of the detection element 16; a metal terminal 33 of an internal ceramic heater 30; leads 34, 36, 38, and 39 respectively connected to metal terminals 28, 32, and 33, and the ceramic heater 30; and housings 40 and 42 for protecting the terminals 28, 32, and 33.

In this oxygen sensor, an oxygen partial pressure signal generated between the two porous electrodes 12 and 14 of the detection element 16 is outputted from the leads 34 and 36 via the metal terminal 28 for the external electrode 12 and the metal terminal 32 for the inner electrode 14 respectively. The oxygen sensor can thus accurately generate the oxygen partial pressure signal without being influenced by noise from an ignition plug or from the ground voltage, compared to another oxygen sensor in which an external porous electrode of a detection element is grounded to the exhaust system via a metal member. An example of the latter type of oxygen sensor is Japanese Patent Publication No. S59-41952.

The above oxygen sensor, however, has the following problem. When a fuel excess period temporarily occurs owing to an application of an accelerator, the carbon particles that are produced adhere to and accumulate on a surface S of the insulating spacer 20 and surfaces of other components, thus causing the deterioration of the insulation between the porous electrode 12 of the detection element 16 and the metal member 18. When the insulation deteriorates, the oxygen partial pressure signal might not be accurately detected due to the noise from an ignition plug or a potential difference from the ground. The carbon particles accumulate on the above site because the temperature is low at the metal member 18 side of the detection element 16. The temperature is comparatively high at the tip of the detection element 16, thereby allowing the carbon particles to be burned off.

SUMMARY OF THE INVENTION

One object of the invention is thus to provide an oxygen sensor that accurately detects an oxygen partial pressure for a long time period.

Another object of the invention is to provide an oxygen sensor in which insulation between an electrode of a detection element and a metal member does not deteriorate even if carbon atoms adhere to and accumulate on the insulating material.

These and other related objects are realized by an oxygen sensor including: a detection element with electrodes, at least one of which is exposed to the atmosphere, for detecting an oxygen partial pressure of the surrounding atmosphere; a metal member insulated from the electrodes, for containing the detection element; an insulating spacer between the detection element and the metal member for supporting the detection element; and an insulating layer for covering the surface of a recess defined by the detection element, the metal member, and the insulating spacer.

The detection element may be of any type with electrodes on its surface: for example, a test-tube shaped one made of the oxygen-ion-conducting solid electrolyte used in Japanese Patent Application No. S61-146210; a cylinder type formed by covering an insulating cylinder having an air-introducing hole, surrounded by an oxygen-ion-conducting solid electrolyte tube; and a semiconductor one using an oxide such as $TiO_2$.

The insulating layer may be any heat-stable one: for example, a heat-stable insulating paint mainly consisting of $Al_2O_3$, $SiO_2$, etc. The insulating layer is easily formed by applying and drying the insulating paint.

In the present invention, since the insulating layer covers the surface of the recess defined by the detection element, the metal member, and the insulating spacer, even if carbon particles adhere to and accumulate on the insulating spacer, the insulation between the outer surface electrode of the detection element and the metal member will not deteriorate. The oxygen sensor of the invention can thus accurately detect the oxygen partial pressure for a long time.

DETAILED DESCRIPTION OF A PREFERRED EMBODIMENT

A preferred embodiment of the invention is now described. Since there may be many modifications without departing from the scope of the invention, the embodiment below is not intended to limit the scope of the claims, but is intended to illustrate the invention more clearly.

Figure 1:
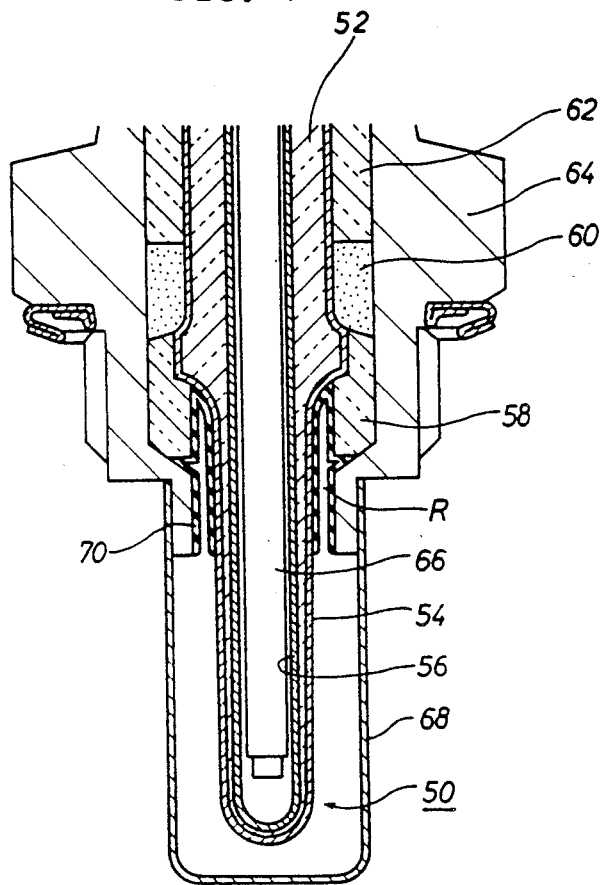
FIG. 1 is a sectional view illustrating an embodiment of the present invention.

The embodiment is an oxygen sensor with a test-tube shaped detection element 50, as shown in FIG. 1.

The detection element 50 includes a test-tube shaped oxygen-ion-conducting solid electrolyte 52 made of a $ZrO_2$ solid solution, and a pair of porous electrodes 54 and 56 provided on face of the either oxygen-ion-conducting solid electrolyte 52. A metal member 64 supports the detection element 50 with an insulating ceramic spacer 58, packing talc powders 60, and a ceramic sleeve 62. The detection element 50 outputs an oxygen partial pressure signal via metal terminal and leads (not shown) in the same manner as the oxygen sensor shown in Japanese Patent Application No. S61-146210.

The oxygen sensor of the present embodiment has a ceramic heater 66 and a protection tube 68, and further includes an insulating layer 70 made of a heat-stable insulating paint covering the surface of a recess R defined by the detection element 50, the metal member 64, and the insulating spacer 58. The insulating layer 70 is formed by injecting the heat-stable insulating paint (BOND X86, a trademark of NISSAN KAGAKU) in the recess R with an injection needle, removing the excess with the needle, and then drying the injected paint.

Figure 2:
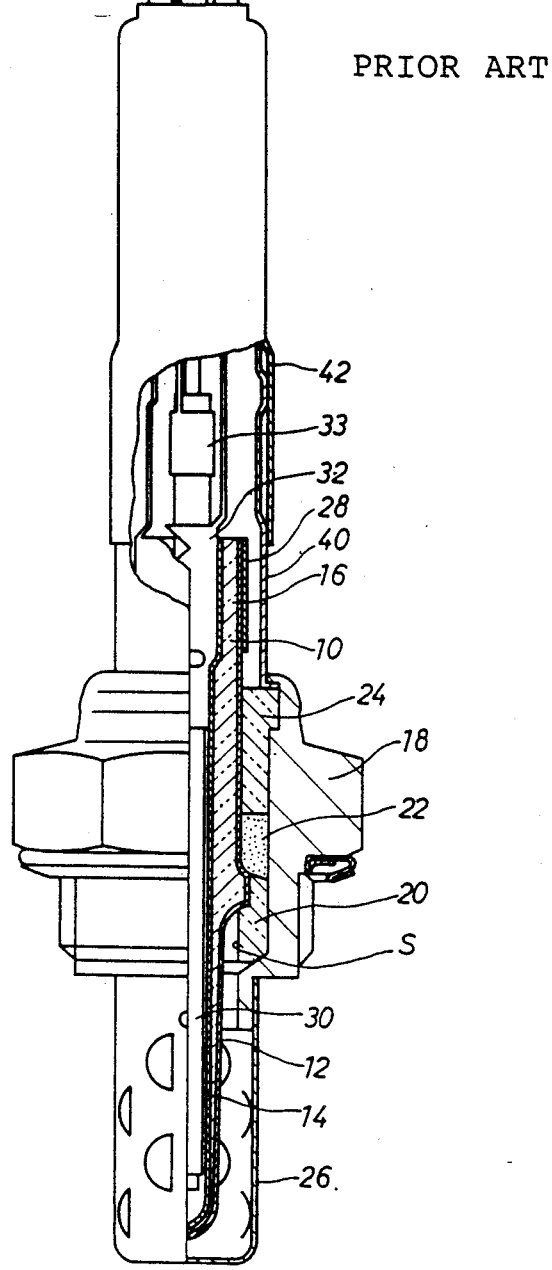
FIG. 2 is a partially sectional view illustrating a prior-art oxygen sensor.

A duration test of the oxygen sensor is performed under the following conditions. The insulation resistance between the external electrode 54 of the detection element 50 and the metal member 64 is measured before and after the test. For the comparison, the same measurement is done on the general oxygen sensor (shown in FIG. 2), which does not have the insulating layer. Table 1 shows the mean value of each measurement.

TABLE

| Conditions for Duration Test | |
|---|---|
| atmosphere | excess fuel (the air/fuel ratio A/F = 9) |
| temperature | 800° C. |
| time period | 100 hr |
| number of samples | 5 each |

| insulating layer | the mean insulation resistance before the test (MΩ) | the mean insulation resistance after the test (MΩ) |
|---|---|---|
| with | 9.0 | 1.2 |
| without | 9.0 | 0.005 |

While the all values measured after the test are less than or equal to 10KΩ in the general oxygen sensor, those in the oxygen sensor of the present embodiment are greater than or equal to 1M. As shown in Table 1, the decline of the insulation resistance can be drastically reduced by the insulating layer.

The oxygen sensor of the present embodiment outputs an oxygen partial pressure signal generated between the two porous electrodes 54 and 56 of the detection element 50, from the leads (not shown) via the metal terminals (not shown). The oxygen sensor can thus accurately detect the oxygen partial pressure signal without being influenced by noise from an ignition plug or by a potential difference from the ground voltage. Since the oxygen sensor further includes the insulating layer 70 for covering the surface of the recess R defined by the detection element 50, the metal member 64, and the insulating spacer 58, the drop of the insulation resistance between the external electrode 54 and the metal member 64 caused by adherence and accumulation of carbon particles can be prevented to a great extent. The oxygen sensor of the present invention thus maintains its stable performance for a long time.

What is claimed is:

1. A solid electrolyte oxygen sensor comprising:
    a detection element comprising a solid electrolyte and inner and outer electrodes coupled to said solid electrolyte, at least one of which is exposed to the atmosphere, for detecting an oxygen partial pressure for the surrounding atmosphere;
    a metal member insulated from the outer electrode of the detection element for containing the detection element;
    an insulating spacer provided between the outer electrode of the detection element and the metal member for supporting the detecting element; and
    heat-stable insulating layer means covering the surface of a recess defined between the detection element on one side and the metal member and the insulating spacer on the other side for preventing deterioration of insulation between said electrodes and said metal member.

2. An oxygen sensor according to claim 1, in which the solid electrolyte is an oxygen ion-conducting solid electrolyte.

3. An oxygen sensor according to claim 2, in which the detection element has the shape of a test-tube.

4. An oxygen sensor according to claim 2, in which the detection element is cylindrical.

5. An oxygen sensor according to claim 1, in which the insulating layer mainly consists of $Al_2O_3$.

6. An oxygen sensor according to claim 1, in which the insulating layer mainly consists of $SiO_2$.

* * * * *